US006818799B2

(12) United States Patent
Liu et al.

(10) Patent No.: US 6,818,799 B2
(45) Date of Patent: Nov. 16, 2004

(54) PROCESS FOR REMOVING TAR FROM SPENT ACID

(75) Inventors: Richard Wai-Chun Liu, Seabrook, TX (US); Philip Dean Hill, Baton Rouge, LA (US); Thomas Edwin Pruitt, Deer Park, TX (US); Forrest Lee Sanders, Katy, TX (US); Albert Yi Yang, Houston, TX (US)

(73) Assignee: Rhodia, Inc., Cranbury, NJ (US)

( * ) Notice: Subject to any disclaimer, the term of this patent is extended or adjusted under 35 U.S.C. 154(b) by 38 days.

(21) Appl. No.: 10/418,193

(22) Filed: Apr. 17, 2003

(65) Prior Publication Data

US 2004/0210095 A1 Oct. 21, 2004

(51) Int. Cl.$^{7}$ ......................... C07C 29/04; C07C 27/08; C07C 29/06; B01D 1/00; B03D 1/00

(52) U.S. Cl. ....................... 568/895; 568/896; 568/899; 568/913; 568/918; 568/383; 210/703; 210/704; 210/708; 210/709; 210/744; 210/196; 516/41

(58) Field of Search ................................ 568/895, 896, 568/899, 913, 918, 383; 210/703, 704, 708, 709, 744, 196; 516/41

(56) References Cited

U.S. PATENT DOCUMENTS 4,406,760 A 9/1983 Knudsen et al.
5,080,802 A 1/1992 Cairo, Jr. et al.
5,156,745 A 10/1992 Cairo, Jr. et al.
6,197,837 B1 3/2001 Hill et al.
6,245,216 B1 6/2001 Hill et al.

OTHER PUBLICATIONS

Angelidou et al. "The Removal of Emulsified Oil Particles from Water by Flotation," Ind. Eng. Chem. Process Des. Dev., vol. 16, No. 4, 1977.

Encyclopedia of Chemical Technology, 2$^{nd}$ Edition, vol. 13, 333–334., 1987.

*Primary Examiner*—Elvis O. Price
(74) *Attorney, Agent, or Firm*—Ohlandt, Greeley, Ruggiero & Perle, L.L.P.

(57) ABSTRACT

There is a process for removing by-product tar during the manufacture of isopropyl alcohol. The process comprises the following: a) reacting propylene with concentrated sulfuric acid and water to form isopropyl alcohol and a spent acid having a by-product tar; b) capturing at least a portion of the isopropyl alcohol; c) contacting the spent acid with a gas in bubble form; d) allowing a least a portion of the tar to separate from the remainder of the spent acid to form a layer of tar and a layer of cleaned acid solution; e) capturing the tar; and h) recycling the cleaned acid solution to step a) as a source of sulfuric acid. There is also a process for removing by-product tar during the manufacture of methyl ethyl ketone. The process is substantially the same except that 1-butene is substituted for propylene. There is also a process for removing tar from a spent acid.

21 Claims, 8 Drawing Sheets

Spent Acid before Cleaning 500X magnification @170°F

Spent Acid After Cleaning 500X magnification @170°F

FIGURE 4

Spent Acid before Cleaning 500X magnification @306°F

Spent Acid after Cleaning 500X magnification @306°F

Spent Acid before cleaning
500X magnification @ 320° F

Spent Acid after cleaning
500X magnification @ 320° F

PROCESS FOR REMOVING TAR FROM SPENT ACID

BACKGROUND OF THE INVENTION

1. Field of the Invention

The present invention relates to a process for removing tar from a spent acid. The present invention further relates to a process for removing by-product tar during the manufacture of isopropyl alcohol and methyl ethyl ketone.

2. Description of the Prior Art

Acids have been used in industrial hydrocarbon refining processes. For example, in indirect hydration processes for manufacturing isopropyl alcohol (IPA) and methyl ethyl ketone (MEK), concentrated sulfuric acid (e.g. 60% to 95% by weight) is employed as a catalyst for reactants. For economic reasons, sulfuric acid is captured and reused in the process. The sulfuric acid to be reused is in a dilute form referred to in the industry as "spent acid." The spent acid is refined or concentrated by boiling off water, typically in a heater or heat exchanger.

A common problem encountered during the concentration of spent acid is the fouling of heater or heat exchanger surfaces. Fouling comes from the presence of dispersed tar, a reaction by-product, in the spent acid. Fouling necessitates more frequent cleaning and maintenance of the heat exchanger and reduces heat exchange efficiency.

U.S. Pat. No. 4,406,760 relates to the use of electrolytic process for treating sulfuric acid streams. Impurities are electrolytically oxidized. A disadvantage of the electrolytic process is the formation of hydrogen bubbles, which causes industrial hygiene and safety concerns.

Ind. Eng. Chem., Process Des. Dev., vol. 16, No. 4, 1977, discloses the use of air sparging, with cationic/nonionic surfactants to separate, low viscosity oil dispersions from water and sea water.

U.S. Pat. Nos. 5,080,802 and 5,156,747 disclose the use of a gas-producing eductor and coalescer to separate oil and particulate materials from liquids:

It would be desirable to have a process for removing tars from spent acid. It would further be desirable to have a process for removing tars from spent acid in indirect hydration processes for manufacturing IPA and MEK.

SUMMARY OF THE INVENTION

It is an object of the present invention to have a process for removing tar from spent acid.

It is an object of the present invention to have a, process for removing by-product tar from spent acid, in the manufacture of IPA and MEK.

According to this and other objects of the, present invention, there is a process for removing by-product tar during the manufacture of isopropyl alcohol. The process comprises the following a) reacting propyl with concentrated sulfuric acid and water to form isopropyl alcohol and a spent acid having a by-product tar therein; b) capturing at least a portion of the isopropyl alcohol c) contacting the spent acid with a gas in bubble form; d) allowing at least a portion of the tar to separate from the remainder of the spent acid to form a layer of tar and a layer of cleaned acid solution; e) capturing tar from the tar layer and disposing of it; f) capturing cleaned acid solution from the cleaned acid solution layer; and g) recycling the cleaned acid solution to step a) as a source of acid.

Still further according to this and other objects of the present invention, there is a process for removing by-product tar during the manufacture of methyl ethyl ketone. The process is substantially the same as the foregoing except that 1-butene is substituted for propylene.

Yet further according to this and other objects of the present invention, there is a process for removing tar from a spent acid. The process has the following steps: i) contacting the spent acid with a gas in bubble form for a time period sufficient to contact the tar; ii) allowing at least a portion of the tar to separate from the remainder of the spent acid to form a layer of tar; and iii) capturing the tar.

BRIEF DESCRIPTION OF THE DRAWINGS

FIG. 4 is a micrograph (500×) of spent acid before cleaning in Example 2.

DETAILED DESCRIPTION OF THE INVENTION

Figure 1:
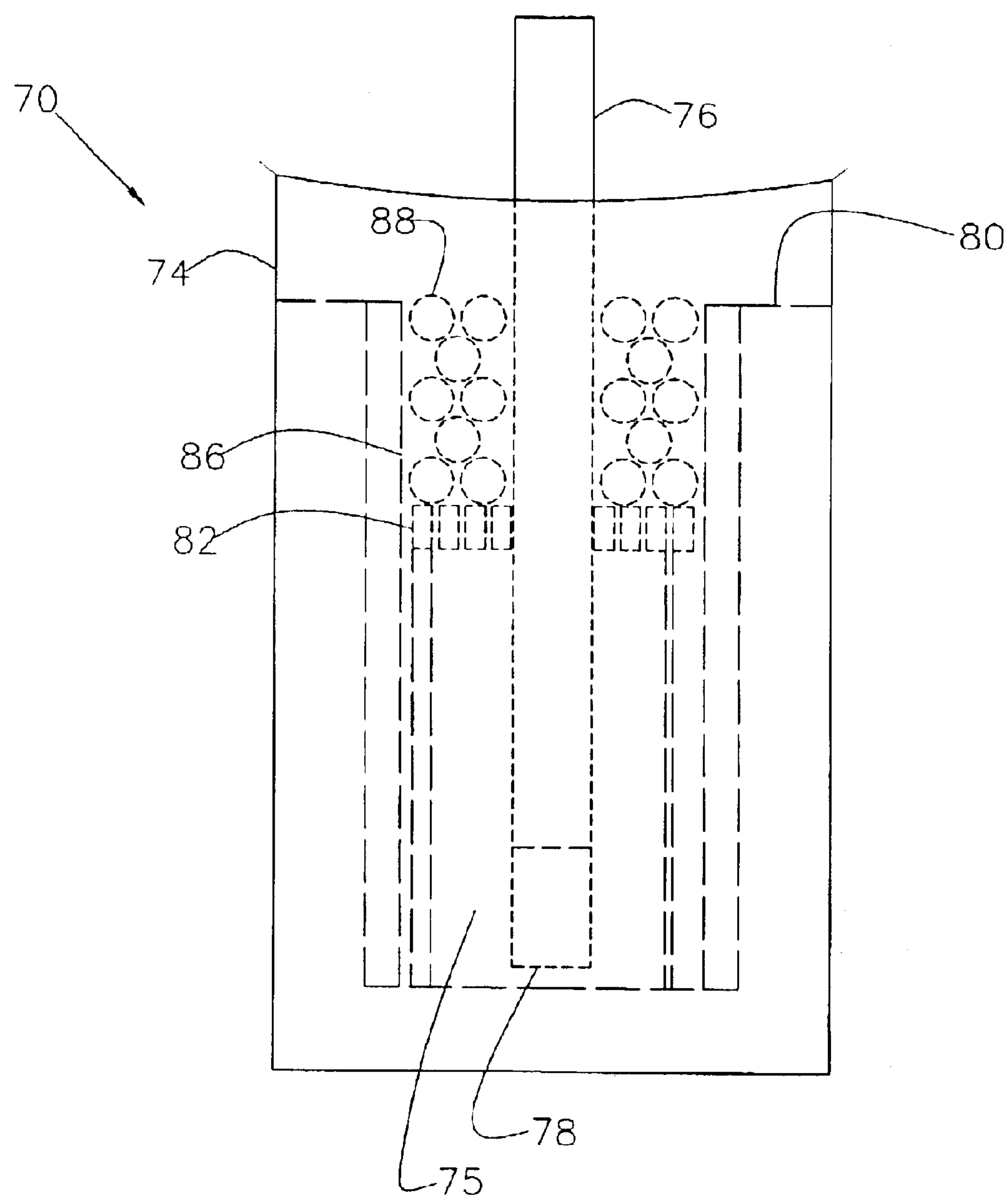
FIG. 1 is a cross-sectional view of yet another embodiment of a gas sparging separation module useful in the process of the present invention. The separation module was employed in Examples 1 and 2

It was found surprising that tar could be removed from the spent acid. It was also found surprising that by-product tar could be removed during the manufacture of MEK and IPA. Tar is removed by introducing into spent acid a gas such that it is dispersed in the form of bubbles. The bubbles contact if the by-product tar and cause it to float and separate as a layer floating on the spent acid. The floating layer is captured and otherwise disposed of. The remainder of the spent acid, the cleaned acid solution is returned in the manufacturing processes as a source of acid. If desired, the cleaned acid solution can be boiled in a heater or heat exchanger to concentrate the acid prior to reuse.

A gas is introduced into the spent acid in the form of bubbles to effect separation of the tar dispersion from the other components of the spent acid. The gas may be introduced into the spent acid by any means known in the art, such as injection or by vacuum. One means for introducing the gas is an eductor, which employs the flow of spent acid therethrough to create a vacuum that draws gas into the spent acid. A preferred means for introducing the gas is blowing the gas through a gas sparger. The size of the bubbles introduced is preferably microscopic, which is typically about 3000 microns or less and most typically about 100 to about 300 microns in diameter. The bubbles are dispersed and allowed to contact the by-product tar for a time period sufficient for tar separation and formation of a tar layer on top of the spent acid. The separation can be carried out over a wide range of temperatures, e.g. typically up to about 350° F. and more typically about 100° F. to about –350° F.

Virtually any gas is useful in the present invention so long as it does not react or cause undesirable chemical byproduct reactions with the spent acid. Useful gases include nitrogen, carbon dioxide, argon, and air. Nitrogen is a preferred gas.

After the gas is introduced into the spent acid, the spent acid may optionally be passed through a static or dynamic mixer to ensure substantially homogeneous dispersion of bubbles therein.

After introduction of gas bubbles, the spent acid having the dispersed gas bubbles therein is allowed to settle to effect separation of the spent acid into a layer or phase of tar and a layer or phase of a cleaned acid solution. Such separation is typically carried out by conveying the gas-laden spent acid to a tank or other container vessel. The retention time of the gas-laden spent acid in the tank or vessel is regulated such that such layering or phase separation has sufficient time to occur. An advantage of the present invention is that separation can take place without the introduction of a surfactant, e.g., a cationic surfactant or a nonionic surfactant, into the spent acid. If desired, a surfactant may be introduced.

The tar layer can be captured or removed from the spent acid by any means known in the art, such as filtration, runoff/overflow trough or paddle action. The cleaned acid solution is then returned as a source of acid or may be concentrated by removal of water by boiling in a heater or heat exchanger and then recycling. The tar layer may be disposed or regenerated to yield sulfuric acid by means known in the art. One means for regenerating sulfuric acid from the tar layer is to fluidize the tar by adding dilute sulfuric acid and a optionally a surfactant. The fluidized tar is incinerated to yield sulfur dioxide. The sulfur dioxide is converted to sulfur trioxide, which is contracted with dilute sulfuric acid to form more concentrated (more enriched) sulfuric acid for reuse as a source or concentrated sulfuric acid. Alternately, the sulfur trioxide may be contacted with water to produce sulfuric acid for reuse. Additional teachings regarding the fluidization and conversion of tar to sulfuric acid are shown in U.S. Pat. Nos. 6,197,837 and 6,245,216 which is incorporated herein by reference.

Spent acid may have acid soluble hydrocarbons dissolved therein and acid-insoluble tars dispersed therein. The present processes can remove a portion of or substantially all the acid insoluble tars. Prior to treatment (cleaning), the spent acid is typically dark, opaque and vary in appearance. After acid-insoluble tars have been removed, the remainder of the spent acid is a cleaned acid solution that is substantially lower in tar content.

Examples of useful commercial separation modules include the Wemco Duperator 1+1 (Baker Hughes Process Systems) ISF-Induced Static Flotation Cell (Baker Hughes Process Systems) and Unicell Vertical IGF (Unicell Technologies).

Flocculating agents or absorbent particles optionally may be employed in the present invention to assist the removal of tar. Absorbent particles are particularly useful. Absorbent particles ray be used in an amount and for a period of time sufficient to contact and absorb additional tar from the spent acid. Typically, the amount of absorbent particles used will be about 0.1 wt % or more, preferably about 0.25 weight percent (wt %) to about 5.0 wt %, more preferably about 0.50 wt % to about 3.0 wt %, and most preferably about 05.0 wt % to about 2.0 wt. % based upon the weight of the spent acid. Useful absorbent particles are carbon black and fumed silica. Carbo black is preferred. Preferred carbon blacks are industrially reinforcing carbon blacks and are activated. Useful carbon blacks have a nitrogen surface area/weight ratio of about 20 to abort 700 $m^2$/gram, preferably about 70 to about 350 $m^2$/gram and most preferably about 80 to about 250 $m^2$/gram. Useful fumed silicas may have hydrophilic (Cab-0-SIL TS-720 by Cabot) or hydrophobic (Cab-0-SIL TS 720 by Cabot) or equivalent surfaces. Preferred surface area/weight ratios are about 100+/−20 $m^2$/gram. As needed filtration and/or centrifugation may be used to separate tar-laden absorbent particles from spent acid and/or tar sludges.

The present invention is particularly useful in cleaning by-product tar from conventional indirect hydration processes for manufacturing isopropyl alcohol (IPA) and methyl ethyl ketone (MEK).

In the manufacture of IPA, propylene is reacted with concentrated aqueous sulfuric acid and water in sequence to form IPA and an acid containing by-product tar dispersion referred to as spent acid. After the first reaction with concentrated sulfuric acid, propylene is converted to propyl sulfate esters. The sulfates are then reacted with water to form IPA. The water reaction is usually carried by steam stripping, which also functions to separate the IPA in an overhead vapor stream. Numerous by-products can be formed, including tar, diisopropyl ether, acetone, propionaldehyde, and polymers of propylene an IPA. By-products can be present in the overhead vapor stream or in the stripper bottoms (liquid stream from stripper). The spent acid typically comprises acid-soluble hydrocarbons and acid-insoluble mixed tars present in the stripper bottoms in the form of a dark dispersion. The spent acid has a brown/black coloration and is usually opaque. Sulfuric acid is present at dilute levels in the spent acid because water has been previously added for the hydration reaction. For reasons of economy, it is desirable to reuse the spent acid by removing tar and processing it to a more concentrated form so that it can be returned for use in reacting with propylene in the first reaction step. Tar is removed from the spent acid in accordance with the methods described herein. Tar removal from the spent acid ensures that fouling in the heater or heat exchanger is reduced or substantially reduced. The resulting cleaned acid solution is then concentrated and returned as a source of acid for the process. Optionally, the tar may be fluidized and thermally treated or regenerated into contracted acid according the methods known in the art. Additional teachings to the indirect hydration process for manufacturing IPA are set forth in the Encyclopedia of Chemical Technology, $3^{rd}$ Ed. Vol. 19, pp. 198–220, which is incorporated herein by reference.

The manufacture of MEK is carried out in a manner substantially the same as the manufacture of IPA except that 1-butene is substituted for propylene. The Shell-Dominguez process is an example of an indirect hydration process for manufacturing MEK. Reaction by-products include tar, butadiene, polybutadiene, 4-vinyl-cyclohexene and 4-phenylcyclohexene. Additional teachings to the process are set forth in the Encyclopedia of Chemical Technology $3^{rd}$ Ed. Vol. 12, pp. 133.

Figure 8:
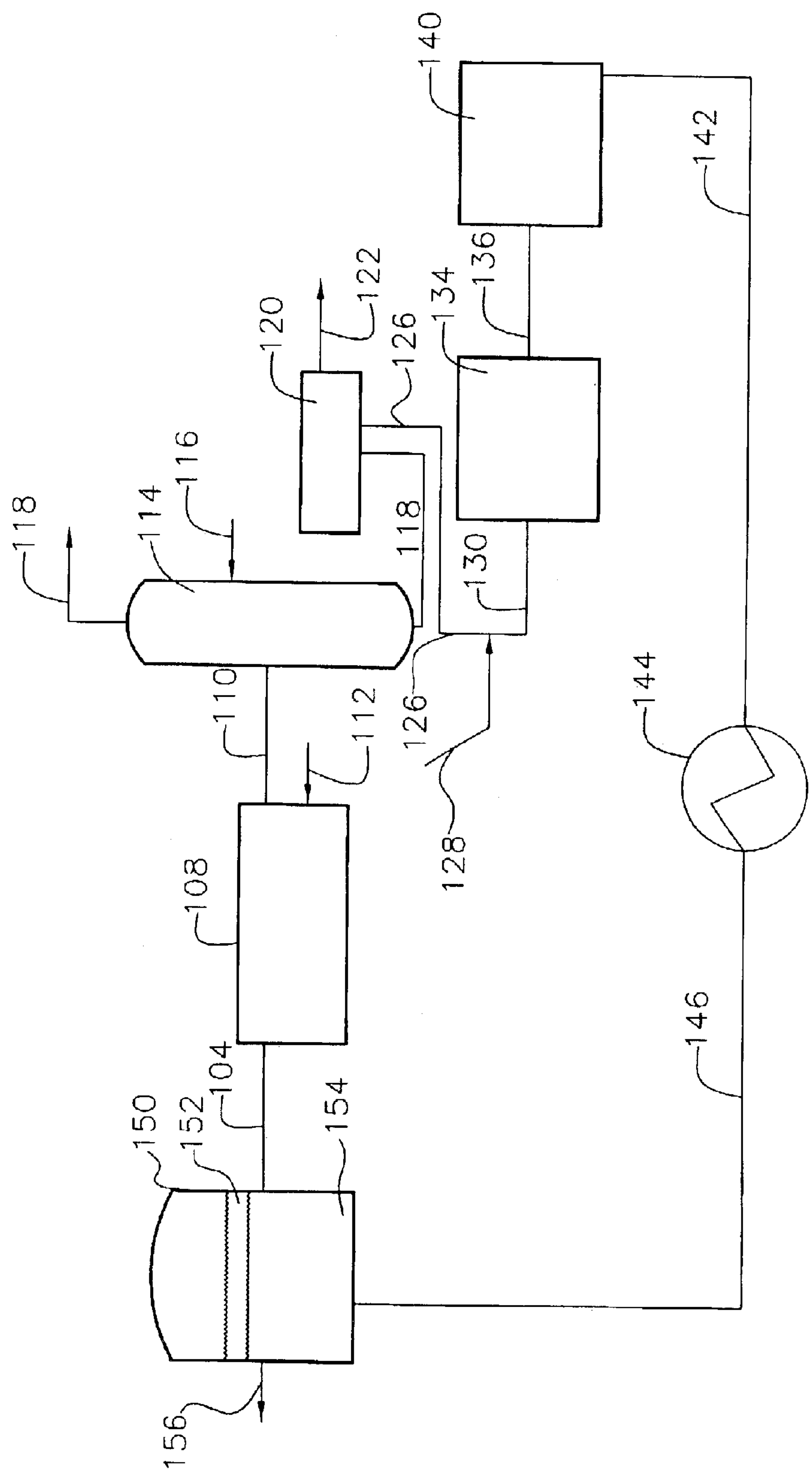
FIG. 8 is a schematic diagram of an indirect hydration process in accordance with the present invention.

A general indirect hydration process is shown schematically in FIG. 8 and is generally referenced by the numeral 100. Concentrated sulfuric acid in conduit 104 is conveyed to absorber 108, where a hydrocarbon feedstock is added via conduit 112. The hydrocarbon feedstock absorbs into the concentrated sulfuric acid in absorber 108 and is conveyed to stripper 114 via conduit 110. Water is added to stripper 114 via conduit 116. The hydrocarbon feedstock reacts with the water to form a product hydrocarbon, which exits stripper 114 via a conduit 118. Spent acid exits the bottom of stripper 114 and is conveyed via conduit 118 to separation module 120. In separation module 120, microscopic bubbles are employed to separate the tar from the remainder of the spent acid. Tar is captured via conduit 122 and stored for subsequent fluidization and thermal regeneration. The remainder of the spent acid takes the form of a cleaned acid solution, which exits module 120 via conduit 126. Makeup concentrated sulfuric acid is added to conduit 126 via conduit 128 to form conduit 130, which leads to heater 134. The cleaned acid solution is heated in heater 134 to drive off part of the water therein to re-concentrate the sulfuric acid. The sulfuric acid concentrate is conveyed to a flash drum 140 via conduit 136. Flash drum 140 lowers the temperature of the boiling acid, removes water vapor and further concentrates the cleaned acid solution. The acid concentrate bottoms from flash drum 140 are conveyed to cooler 144 via conduit 142. Cooler 144 cools the acid concentrate, which is conveyed to a purge tank 150. In purge tank 150, any remaining insoluble tar in the concentrate is allowed to float in a layer 152 on top of the cleaned acid solution layer 154. The acid concentrate is then conveyed to absorber 108 via conduit 104, which was also discussed above. As necessary, floating tar or excess concentrate may be removed from purge tank 150 via conduit 156.

In the following examples, all percentages or parts are by weight unless indicated otherwise.

EXAMPLES

The process of the present invention was used to clean MEK spent acid samples in different separation modules under different temperature conditions. One test was conducted in glass/Teflon™ (polytetrafluoroethylene) separation module at 140° F. to 170° F. (Example 1), a glass/Teflon™ separation module at around 306° F. (Example 2) and a glass sparger separation module at 320° F. (Example 3). Teflon™ is a trademark of E. I. duPont de Nemours & Co.

EXAMPLES

Example 1

Medium Temperature 140° F. to 170° F.

The test in Example 1 was conducted with a Glass/Teflon™ separation module, which is generally referenced by the numeral 70 in FIG. 1. Warm spent acid (140° F. to 170° F.) is introduced into a glass jar 74 up to a level of a filter paper 80, which is doughnut-shaped and composed of glass fiber. Nitrogen gas is introduced into the spent acid through at tube 76 and gas sparger 78 having 20–50 micron holes to form microscopic gas bubbles. Tar dispersion adheres with these gas bubbles and rises inside column 75 into the glass spheres 88. Column 75 has a doughnut-shaped perforated Teflon™ plate 82 designed to support glass spheres 88 as well as to allow gas bubbles and tar to pass through. The tar layer floats over spheres 88 and out onto glass fiber filter paper 80. The cleaned acid is collected from column 15. The thick tar layer has a viscosity of over 10,000, centipoise (Brookfield viscometer at 77° F.).

Samples of the cleaned acid solution were taken at outside of column 75 at time zero and at 6 minutes of module operation. Percent carbon were tested using the Leco CHN (carbon, hydrogen and nitrogen) instrument, % acid were tested by titration and percent (%) water were determined using the potentiometric technique using the 701 KF Titrino tester (Ace Glass Inc.).

TABLE 1

Tar Separation using Glass/Teflon ™ Module at 140° F.–170° F.

| Sample | % acid | % water | % carbon |
|---|---|---|---|
| 0 minute control | 48.1 | 51.9 | 0.56 |
| @6 minute | 48.2 | 51.4 | 0.20 |

Figure 2:
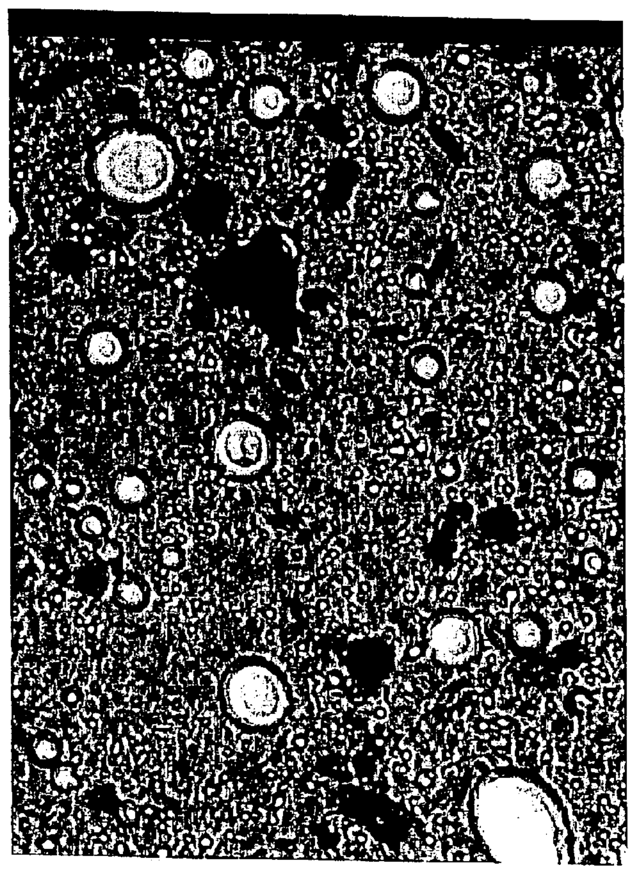
FIG. 2 is a micrograph (500×) of spent acid before cleaning in Example 1.
Figure 3:
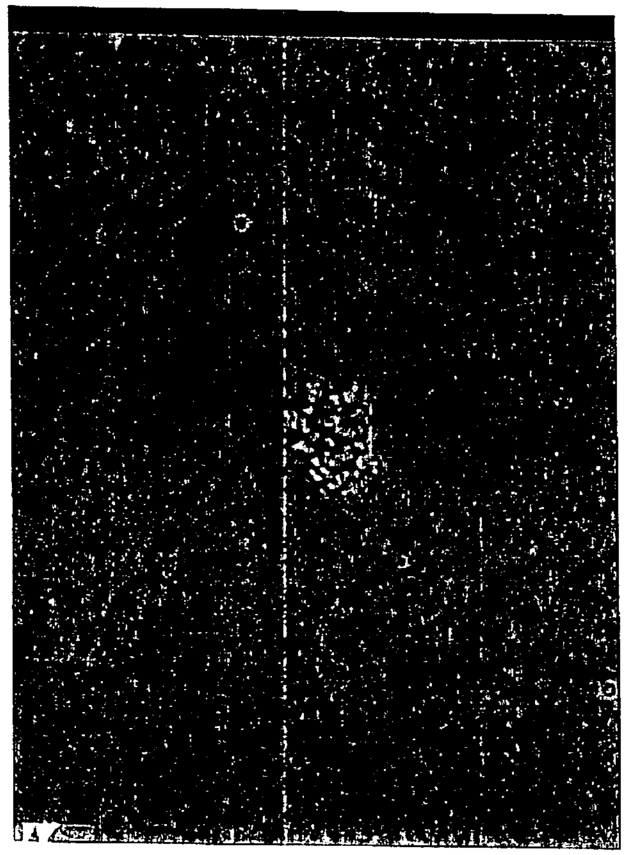
FIG. 3 is a micrograph (500×) of spent acid after cleaning in Example 1.

The percent (%) carbon in the treated 6 minute sample is significantly less than for the untreated control sample. Micrographs (500× magnification) of the control sample and the 6 minute sample can be seen in FIGS. 2 and 3, respectively. Comparing FIGS. 2 and 3, the amount of tar dispersion in the cleaned sample is visibly lower. The cleaned acid is less turbid reflecting reduced amount of tar dispersion.

Example 2

High Temperature—306° F.

The test in Example 2 was conducted with the same separation module (glass/Teflon™ unit) as in Example 1 and was conducted in substantially the same manner as Example 1 except for a different operating temperature.

Column 75 was placed in jar 74 and the jar 74 preheated to 306° F. In a separate jar heated to 306° F., the spent acid and a small amount of tar were mixed together rapidly and added to jar 74. A loose layer of tar was noticed to form rapidly on the surface. Samples were collected near the top and around the middle level of jar 74. Nitrogen gas was passed through sparger 78 at 2 standard cubic feet per hour and cleaned acid samples were collected near the bottom of module 74 at 2 and 5 minutes after initiation of gas flow. Filter paper 78 was placed on top of the glass spheres 88 to collect the tar being separated. A sample was collected at the tar layer and at the bottom of jar 74 for the time 0 to time 5 minute samples. The percent carbon, acid, and water for the samples were tested.

TABLE 2

Tar Separation using Glass/Teflon ™ Module at 306° F.

| Sample | % acid | % water | % carbon |
|---|---|---|---|
| Top Tar Rich Layer | 60.1 | 38.6 | 1.04 |
| 0 minute sample | 61.1 | 38.4 | 0.27 |
| 2 minute sample | 61.7 | 37.9 | 0.28 |
| 5 minute sample | 61.5 | 38.1 | 0.19 |

Figure 4:
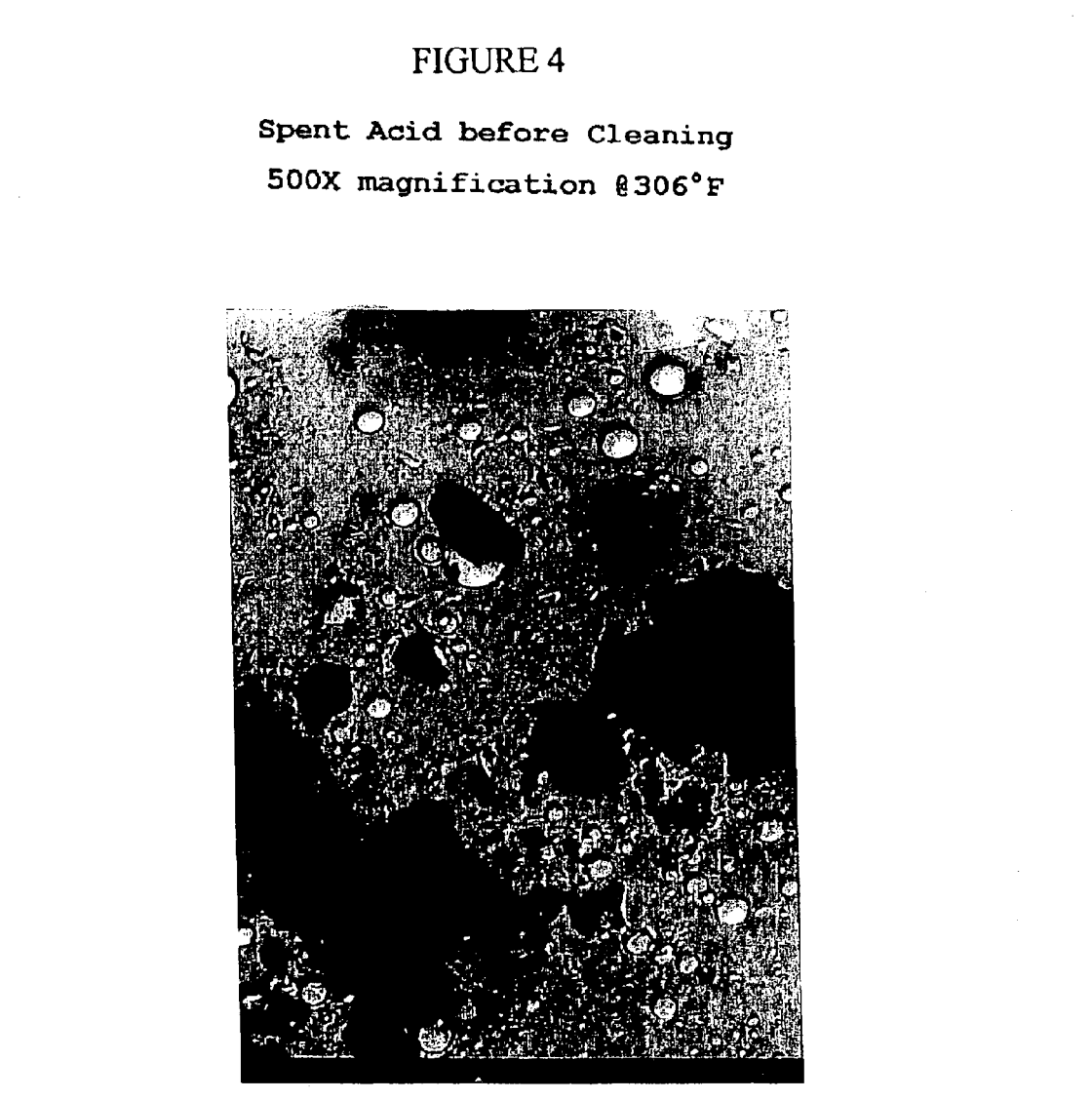
Figure 5:
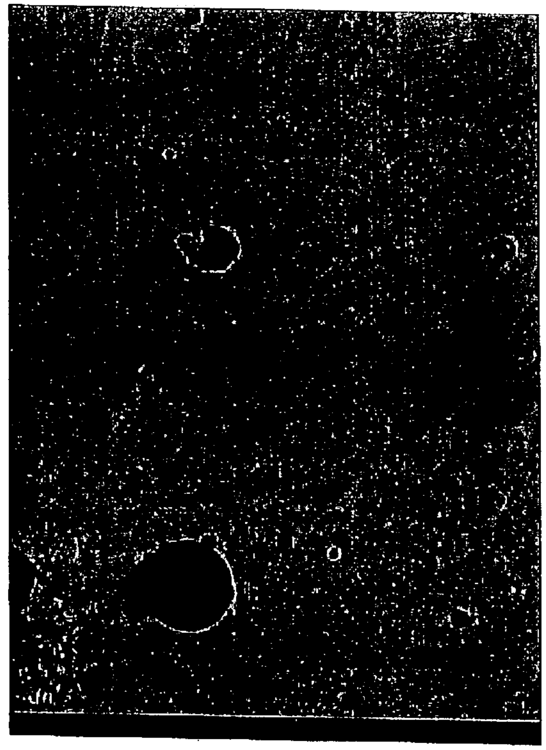
FIG. 5 is a micrograph (500×) of spent acid after cleaning in Example 2.

The initial top tar layer sample had the highest tar content (1.04%) even before the nitrogen sparging was started. The control sample (0-minute) was down to 0.27% carbon shortly before sparging was started. The carbon content was unchanged after 2 minutes of sparging butt was down to 0.19% after 5 minutes. The heaviest tar dispersion was seen to collect quickly at the top (FIG. 4) whereas the tar droplets collected near the bottom were noticeably smaller for the 5 minute sample (FIG. 5.

Example 3

Gas Sparging at 320° F.

This test was conducted with a separation module different than the module employed in Examples 1 and 2. A glass jar was penetrated to 320° F. and warm spent acid (@130° F.) was poured into jar 74 jar. The spent acid was heated to 320° F. under constant stirring. As soon as the equilibrium temperature was reached, nitrogen gas was injected through a glass sparger into the bottom of the jar at about 2 cubic feet/minute. Samples were collected at 0, 5 and 10 minutes at the bottom of jar 74. Results are set forth in Table 3.

TABLE 3

Tar Separation using Glass Sparger at 320° F.

| Time of Sample, (minutes) | % Carbon |
|---|---|
| 0 | 0.5 |
| 5 | 0.35 |
| 10 | 0.32 |

Figure 6:
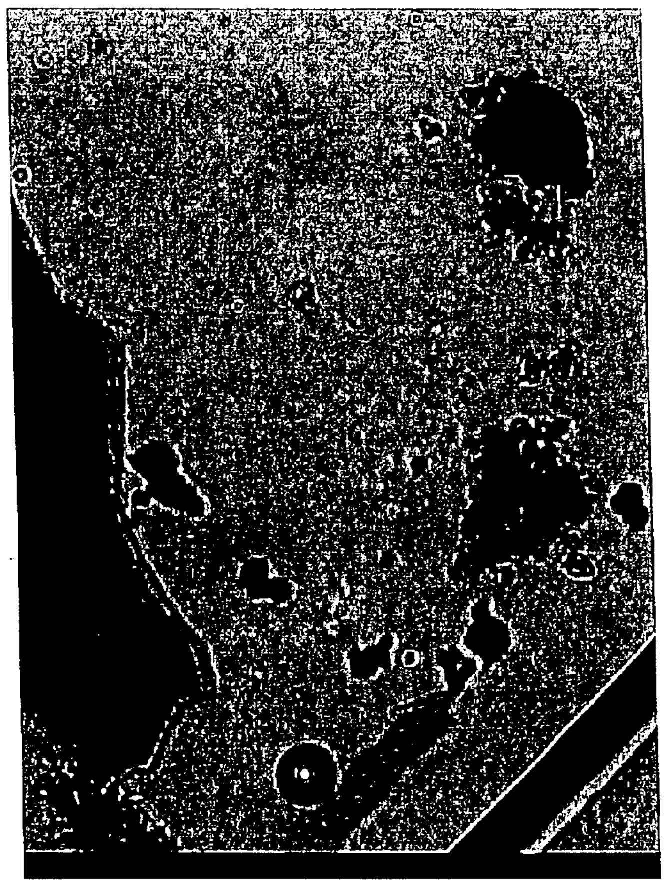
FIG. 6 is a micrograph (500×) of spent acid before cleaning in Example 3.
Figure 7:
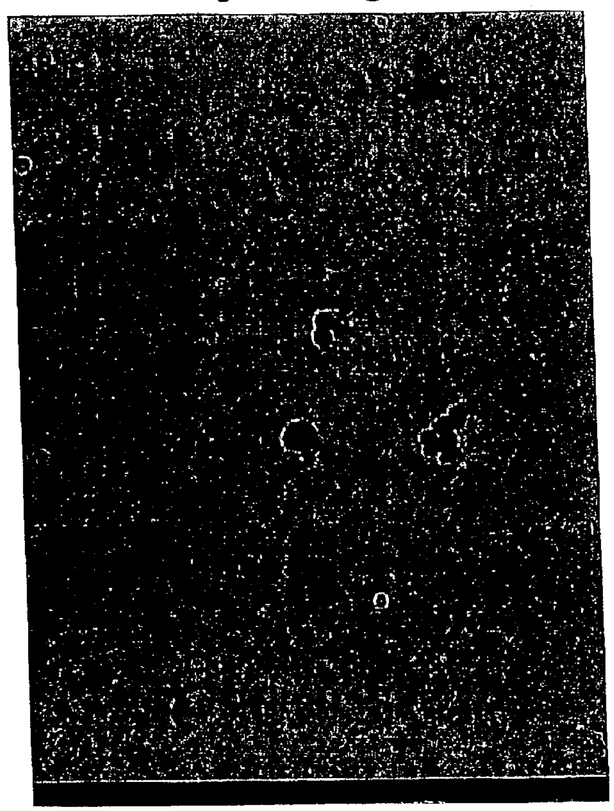
FIG. 7 is a micrograph (500×) of spent acid after cleaning in Example 3.

The initial 0 minute sample exhibited the highest carbon level, whereas the carbon level of the 5 and 10 minute were lower. The 0 minute sample exhibits more visible tar dispersion (FIG. 6) than the 5 minute sample (FIG. 7).

It should be understood that the foregoing description is only illustrative of the present invent. Various alternatives and modifications can be devised by those skilled in the art without departing from the invention. Accordingly, the present invention is intended to embrace all such alternatives, modifications and variances that fall within the scope of the appended claims.

What is claimed is:

1. A process for removing by-product tar during the manufacture of isopropyl alcohol, comprising:

a) reacting propylene with concentrated sulfuric acid and water to form isopropyl alcohol and a spent acid having the by-product tar;

b) capturing at least a portion of the isopropyl alcohol;

c) contacting the spent acid with a gas in bubble form;

d) allowing at least a portion of the tar to separate from the remainder of the spent acid to form a layer of tar on a layer of cleaned acid solution;

e) capturing the tar; and f) returning the cleaned acid solution to step a) as a source of sulfuric acid.

2. The process of claim 1, wherein the cleaned acid solution is heated to form concentrated sulfuric acid prior to return to step a).

3. The process of claim 2, wherein the captured tar is subsequently fluidized by addition of dilute sulfuric acid and a surfactant thereto, and wherein the fluidized tar is incinerated to form sulfur dioxide, and wherein, the sulfur dioxide is converted to sulfur trioxide, and wherein the sulfur trioxide is contacted with dilute sulfuric acid to form an enriched concentrated sulfuric acid for return to step a).

4. The process of claim 1, wherein the bubbles are formed by passing the gas through a sparger.

5. The process of claim 1, wherein the bubble size is about 3000 microns or less.

6. The process of claim 3, wherein the bubble size is about 3000 microns or less.

7. The process of claim 1, wherein the bubble size is about 100 to about 300 microns.

8. The process of claim 1, wherein the gas is nitrogen.

9. A process for removing by-product tar during the manufacture of methyl ethyl ketone, comprising:

a) reacting 1-butene with concentrated sulfuric acid and water to form methyl ethyl ketone and a spent acid having the by-product tar;

b) capturing at least a portion of the methyl ethyl ketone;

c) contacting the spent acid with a gas in the form of bubbles;

d) allowing at least a portion of the tar to separate from the remainder or the spent acid to form a layer of tar and a layer of a cleaned acid solution;

e) capturing the tar; and f) returning the cleaned acid solution to step a), as a source of sulfuric acid.

10. The process of clam 9, wherein the cleaned acid solution is heated to form concentrated sulfuric acid prior to return to step a).

11. The process of clam 10, wherein the captured tar is subsequently fluidized by addition of dilute sulfuric acid and a surfactant thereto, and wherein the fluidized tar is incinerated to form sulfur dioxide, and wherein the sulfur dioxide is converted to sulfur trioxide, and wherein the sulfur trioxide is contacted with dilute sulfuric acid to form an enriched concentrated sulfuric acid for return to step a).

12. The process of claim 9, wherein the bubbles are formed by passing the gas through a sparger.

13. The process of claim 9, wherein the bubble size is about 3000 microns or less.

14. The process of claim 11, wherein the bubble size is about 3000 microns or less.

15. The process of claim 9, wherein the bubble size is about 3000 microns or less.

16. The process of claim 9, wherein the gas is nitrogen.

17. A process for removing tar from a spent acid, comprising:

contacting the spent acid with a gas in bubble form;

allowing at least a portion of the tar to separate from the remainder of the spent acid to form a layer of tar; and capturing the tar.

18. The process of claim 17 wherein the bubbles are formed by passing the gas through a sparger.

19. The process of claim 17, wherein the bubble size is about 3000 microns or less.

20. The process of claim 17, wherein the gas is nitrogen.

21. The process of claim 17, wherein the spent acid is also contacted with absorbent particles.

* * * * *